United States Patent [19]

Sherif et al.

[11] Patent Number: 5,330,944
[45] Date of Patent: Jul. 19, 1994

[54] SULFUR-RESISTANT HYDROGENATION CATALYST AND PROCESS FOR HYDROGENATION USING SAME

[75] Inventors: Fawzy G. Sherif, Stony Point; Willem Vreugdenhil, Katonah, both of N.Y.

[73] Assignee: Akzo Nobel nv, Arnhem, Netherlands

[21] Appl. No.: 9,209

[22] Filed: Jan. 22, 1993

[51] Int. Cl.$^5$ .......................... B01J 27/22; B01J 29/08
[52] U.S. Cl. ............................. 502/64; 502/60
[58] Field of Search ...................... 60/64, 177

[56] References Cited

U.S. PATENT DOCUMENTS

| | | | |
|---|---|---|---|
| 4,325,843 | 4/1982 | Slaugh et al. | 502/177 |
| 5,120,692 | 6/1992 | Beck | 502/60 |

OTHER PUBLICATIONS

Markel and Van Zee, J. of Catalysis 126, 643–657 (1990).
Mozingo et al., J. Amer. Chem. Soc. 67, 2092–2095 (1945).
Hargreaves et al., J. of Catalysis 56, 363–376 (1979).
Lee et al., Applied Catalysis, 19, 207–210 (1985).
Dockner, Angew Chem. Int. Ed. Engl. 27, 679–682 (1988).

*Primary Examiner*—Carl F. Dees
*Attorney, Agent, or Firm*—Richard P. Fennelly; Louis A. Morris

[57] ABSTRACT

Tungsten carbide/zeolite catalysts useful in the hydrogenation of unsaturated sulfur containing compounds and in particular in the production of tetrahydrothiophene are provided.

Also provided is a process for the production of tetrahydrothiophene from thiophene using the tungsten carbide/zeolite catalysts taught, which effects the selective production of tetrahydrothiophene without producing large quantities of $H_2S$ and unwanted hydrocarbons.

13 Claims, No Drawings

SULFUR-RESISTANT HYDROGENATION CATALYST AND PROCESS FOR HYDROGENATION USING SAME

BACKGROUND OF THE INVENTION

The present invention relates to a tungsten carbide/zeolite catalyst which has been found to be effective as a hydrogenation catalyst.

More specifically, the present invention relates to a tungsten carbide/zeolite catalyst which has been found to be effective as a hydrogenation catalyst in the conversion of unsaturated sulfur containing compounds to saturated sulfur containing compounds, such as in the conversion of thiophene to tetrahydrothiophene.

There exist known catalysts which are capable of converting sulfur containing unsaturated compounds including thiophene in the presence of $H_2$ to yield principally $H_2S$ and hydrocarbons as the main products. Generally, however, little or no tetrahydrothiophene is formed using such accepted catalysts in the conversion of thiophene. For example, using such known catalysts, amounts in the order of 1-2% of tetrahydrothiophene may be produced.

Catalysts which have been heretofore available are primarily designed for the hydrodesulfurization of feed stocks in the petrochemical industry. The main hydrocarbons formed are olefinic in nature, indicating that the reaction mechanism involves mainly breaking the C—S bond into $H_2S$ and olefins, with lesser hydrogenation activity leading to tetrahydrothiophene and parafins. See for example (J. of Cat. 126,643 (1990).

Other known catalysts that could be employed to reduce sulfur containing components without breaking the C—S bond are palladium on carbon or palladium on barium sulfate, (Mozingo, et al. J. Amer. Chem. Soc., 67, 2092 (1945). However, this reduction reaction is carried out in the presence of mineral acid and can only be used in single batches due to sulfur poisoning of the palladium.

Catalysts such as $Mo_2N$ have also been reported as hydrodesulfurization catalysts, (Markel & Van Zee, J. of Cat., 126, 643 (1990). Using such a catalyst the thiophene cleaves at the C—S bond. The main hydrocarbon products from this reaction are unsaturated olefinic isomers.

Tetrahydrothiophene is a commercial material employed primarily for odorizing household cooking gas in order to alert persons for safety reasons in case of gas leakage. Derivatives of tetrahydrothiophene are also used in the manufacture of pharmaceuticals.

A tungsten/zeolite catalyst has been found which is effective in the hydrogenation of unsaturated sulfur containing compounds and particularly in the selective hydrogenation of thiophene to tetrahydrothiophene, that is to say, without appreciably breaking the C—S bond, according to the following:

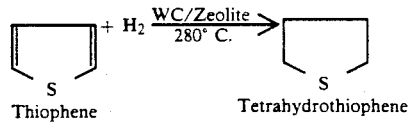

Thiophene      Tetrahydrothiophene

Various references exist in the prior art of which the applicants are aware which relate to the hydrogenation of thiophenes. The most significant of these are the following:

Hargreaves et al (J. of Catalysis 56,363-376 (1979), teach that the hydrogenation of thiophene occurs prior to C—S bond cleavage and that both effects are promoted by Co.

Lee et al (Appl. Cat. 19,207-210 (1985) teaches the effects of thiophene hydrodesulfurization over unsupported molydenum carbide.

Dockner (Angew. Chem., Int., Ed. Engl. 27,679-682 (1988), deals with the hydrogenation of olefins and ureas with technical white oil and activated carbon, amongst other reactions pertinent to the conversion of various hydrocarbons available from petroleum and natural gas as raw materials.

Beck, U.S. Pat. No. 5,120,692 which issued on Jun. 9, 1992, is directed to molecular sieves coated with non-oxide ceramics, which are indicated as being potentially useful as hydrogenation catalysts when used in conjunction with a hydrogenating component such as, among others, tungsten.

These references, however, teach nothing with regard to the specific advantages to be achieved via the utilization of a tungsten carbide/zeolite catalyst according to the present invention, especially in the hydrogenation of thiophene.

The shortcomings of the prior art catalysts noted above are overcome by using the catalyst described in the present invention which allows one to effect the hydrogenation of unsaturated sulfur containing compounds and to effect the production of tetrahydrothiophene in substantial quantities directly from thiophene, without producing the large quantities of $H_2S$ and hydrocarbon by-products which have heretofore been the result of such reactions using available prior art catalysts.

It is therefore the object of this present invention to provide for a novel hydrogenation catalyst.

It is a further object of the present invention to provide a process for the hydrogenation of unsaturated sulfur containing compounds without substantially cleaving the C—S bonds present in such compounds.

It is also an object of the present invention to provide an improved process for the selective production of tetrahydrothiophene directly from thiophene.

Lastly, it is an object of the present invention to provide an improved process for the production of tetrahydrothiophene using the catalyst of the present invention to selectively produce such tetrahydrothiophene with substantial yield, directly from thiophene.

These and other objects of the invention will be reflected in the course of the following more detailed discussion.

SUMMARY OF THE INVENTION

According to the present invention, there is provided tungsten carbide/zeolite catalysts for use in the hydrogenation of unsaturated sulfur containing compounds to produce saturated sulfur containing hydrocarbons and more particularly in the production of tetrahydrothiophene directly from thiophene, and a process for using same.

The catalysts of the present invention have been found to be particularly beneficial in the hydrogenation of thiophene to allow the selective production of tetrahydrothiophene without resulting in the production of substantial quantities of undesirable $H_2S$ and hydrocarbons.

The primary advantage of the catalysts of the present invention therefore lies in the ability to directly produce tetrahydrothiophene from thiophene in substantial quantities, which provides one with the ability to obtain tetrahydrothiophene at lower costs and with less processing than has been heretofore possible using known prior art catalysts.

The use of the process of the present invention to hydrogenate thiophene in order to obtain tetrahydrothiophene and/or to hydrogenate other sulfur containing compounds has the advantage of resulting in the production of significantly less $H_2S$ and other noxious by-products, therefore providing a process which is environmentally cleaner and one which requires the use of less clean up processing then would otherwise be required.

These and other features and advantages of the present invention will be more readily appreciated from the following more detailed description of the invention.

DETAILED DESCRIPTION OF THE INVENTION

The tungsten carbide/zeolite catalysts of the present invention can be prepared by a variety of means.

Generally, the tungsten carbide/zeolite catalysts of the present invention may be prepared using any one of a number of well known catalyst preparation methods so long as the following parameters are met:

The resultant catalyst produced will generally contain approximately 9.8% tungsten carbide as tungsten metal on the zeolite. The tungsten carbide may vary between 1% and 50% as tungsten metal. The catalyst shall have a pore structure and morphology which permits the flow of thiophene without cleaving the C—S bond. The zeolite, which functions as a support, may be admixed with a minor amount (for example, about 20%) of alumina to facilitate extrusion or shaping of the resulting blend. The zeolite/ $Al_2O_3$ ratio in such a blend may vary from 90/10 to 10/90 and preferably be between 60/40 and 90/10, with 80/20 being most preferred. The surface area may vary from about 30–800 $m^2/g$. The silica content of the blend may vary between from about 5–80%. The preferred zeolite will contain 80% silica, and have a surface area of approximately 840 $m^2/g$.

The deposition of the active metal carbide on the support comprising the zeolite can be done using techniques known to persons of ordinary skill in the art, such as by the deposition and pyrolysis of tungsten carbonyl or the use of other chemical precursors (e.g. the reaction of tungsten chloride with guanidine, followed by calcining of the resulting tungsten-containing carbon atom-containing composition).

It is also within the scope of the present invention to utilize co-extrusion techniques known to persons of ordinary skill in the art in the preparation of one or more of the component portions of the subject catalyst. For example, the combination of zeolite support and active carbide material can be formed by co-extruding the respective components. Impregnation and co-extrusion techniques can be combined, as would be apparent to one skilled in this art, in order to form the complete catalyst configuration.

Generally speaking, it has been found that the catalyst compositions which are the subject of the present invention may be effectively employed to achieve the desired hydrogenation of thiophene to selectively produce tetrahydrothiophene at temperatures from about 200° to 500° C., with temperatures of about 250° C. being preferred. Generally, flow rates of from about 2–100 cc/min, with a flow rate of about 10 cc/min being preferred, per catalyst volume of about 0.5 to 50 cc, preferably about 1 cc. can be employed.

Pressures of from about 1 atmosphere to about 100 atmospheres, will generally be employed, with about 1 atmosphere being preferred. $H_2$/thiophene ratios of from about 20/1 to 4/1 are generally employed, with a ratio of 10/1 being preferred.

In one specific embodiment of the present invention, a zeolite was made by extruding a mixture of Y zeolite and 20% $Al_2O_3$. The extrudates contain 33.8% $Al_2O_3$, 64.6% $SiO_2$. The surface area was 649 $m^2/g$ and pore volume 0.72. The extrudates were either impregnated with a solution of, or a molten mixture of, $WCl_6$ and guanidine. HCl, then calcined at 750° C. to give a black uniform extrudate. If desired, other carbon-nitrogen compounds, such as melamine can be substituted for guanidine in the previously described preparation.

When $H_2$ and thiophene were passed over such a catalyst at the rather low temperatures of 250°–290° C., the thiophene conversion was found to be 22–44%. Selectivity to tetrahydrothiophene was 92–94%.

It is known in the art that conversions can be increased to almost 100% by changing the configuration of the reactor, such as by increasing the catalyst volume compared to gas flows. However, the high selectivity at relatively low temperature which is an important contribution of this invention is not otherwise attainable using known prior art techniques.

In another embodiment of the present invention using the claimed catalyst, the continuously unconverted thiophene may be recycled, maintaining the low reaction temperature, and 92–94% tetrahydrothiophene continuously separated from the product stream.

The foregoing discussion of the present inventions will be further illustrated by the following specific examples.

EXAMPLES

EXAMPLE I

This Example describes the preparation of the catalyst of the present invention.

A precursor solution was prepared by first dissolving 8.6 g of guanidine hydrochloride, 0.09 mole, in 75 cc of absolute ethanol, then adding slowly 12 g of $WCl_6$, 0.03 mole, over ten minutes with intermittent cooling of the solution until the $WCl_6$ had dissolved. The resulting solution was brown. This solution was added slowly to zeolites that had been precalcined under $N_2$ at 750° C. for seven and one-half hours. The solution (37.5 cc) was added to 35 g of zeolite, i.e., 1/16" extrudates Type 5A molecular sieve from Fisher. This gave a wet product that was dried under $N_2$ and then calcined to 750° C. over seven and one-half hours and held at 750° C. for two hours, also under $N_2$. The resulting catalyst composition is referred to as "Catalyst A". In a second experiment, 37.5 cc of the solution of the precursor was added to 28 g of another zeolite-containing composition, 1/16" extrudates, 80% zeolite Y admixed with 20% alumina, from Akzo Chemicals, b.V. The wet extrudates were treated as above. The final catalyst from this second run is referred to as "Catalyst B". The properties of the zeolites are summarized below:

|  | Catalyst A | Catalyst B |
|---|---|---|
| Composition | 100% zeolite A | 80% zeolite Y + 20% $Al_2O_3$ |
| Effective pore size, | 5 Å | 7 Å |
| Pore volume, Hg | — | 0.72 |
| SA ($m^2/g$) | — | 649 |
| % $SiO_2$ | — | 64.6 |
| % $Al_2O_3$ | — | 33.8 |

EXAMPLE II

Catalysts A and B from Example 1 were evaluated for their conversion of thiophene in this Example. A stream of $H_2$ gas was bubbled through a reservoir containing thiophene at room temperature. The saturated gas was then passed over 1.0 g of crushed catalyst placed in a micro reactor, Autoclave Engineers, heated at 450°-260° C. The respective catalysts were preheated at 550° C. and were exposed to $H_2$ for sixteen hours for activation before testing. The product gas in each run was sampled by a gas chromatograph. The results showed that thiophene was converted to tetrahydrothiophene with high selectivity, especially with Catalyst B. Other products were hydrocarbons resulting from hydrode-sulfurization $C_1$ to $C_4$. The results are given in Tables 1 and 2 which follow:

TABLE 1

Catalytic Activity of Catalyst A

| Temperature (°C.) | % Conversion of Thiophene | Cumulative Time on Stream, Hrs. | % Tetrahydro-thiophene in Product |
|---|---|---|---|
| 332 | 51 | 1 | 9 |
| 289 | 30 | 2 | 35 |
| 260 | 12 | 2.5 | 68 |
| 228 | 8 | 3.0 | 75 |
| 222 | 5 | 3.5 | 72 |

TABLE 2

Catalytic Activity of Catalyst B

| Temperature (°C.) | % Conversion of Thiophene | Cumulative Time on Stream, Hrs*. | % Tetrahydro-thiophene in Product |
|---|---|---|---|
| 331 | 63 | 11 | 74 |
| 287 | 44 | 15 | 93.4 |
| 253 | 22 | 17 | 92.0 |

*Cumulative times include 8 hours of pre-exposing catalyst to thiophene prior to activation with hydrogen. Longer times on stream reflect greater confidence in the performance of the catalyst and confirm that the catalyst did not coke or get poisoned over time.

The results show that tetrahydrothiophene was the major product of this reaction, under certain reaction conditions.

EXAMPLE III

This Example shows the utility of the catalyst B described in Example II, upon scaling-up from 1 gram to 5 grams. In a macro 100 ml reactor, made by Autoclave Engineers, 5 g of catalyst B were loaded, then activated with hydrogen at 500° C. for 16 hours. The time of activation was not critical and could be less than 16 hours. The 16 hours was only made for convenience since it reflects an overnight operation. The catalyst was then sulfided by a stream containing 9.5% thiophene in hydrogen for 24 hours, 10 cc/minute, at room temperature to insure compatability of the catalyst with the reaction system. This time period was not essential to the performance of the catalyst and could vary from 0-24 hours. Catalyst testing was then made by analyzing the feed gas and the product gas mixtures using an on-line gas chromatograph precalibrated with thiophene and tetrahydrothiophene. At each temperature, arbitrarily chosen for testing, the catalyst was exposed to the thiophene gas stream for 1-2 hours for equilibration before sampling. Several samples were taken at each temperature to ensure that the results are consistent and represent the steady state at this temperature. Time intervals between testing are arbitrarily chosen and only reflect work schedule. Longer times on stream reflect more confidence in the performance of the catalyst and confirm that the catalyst did not coke or get poisoned.

The results of testing are represented by the following data:

TABLE 3

| Temperature (°C.) | % Conversion of Thiophene | Cumulative Time on Stream, Hrs. | % Tetrahydro-thiophene in Product |
|---|---|---|---|
| 333 | 90.7 | 3 | 23.8 |
| 289 | 94.4 | 8 | 68.8 |
| 256 | 85.0 | 11 | 85.0 |
| 228 | 57.0 | 14 | 89.2 |

The results show that at the desirable lower temperatures, the selectivity to tetrahydrothiophene was enhanced. These results depend upon the flow rate, the concentration of thiophene in hydrogen, the packing of the catalyst bed, and the pressure of the reaction. Higher conversion and selectively values could be achieved by optimizing those conditions.

EXAMPLE IV—COMPARATIVE

This Example is similar to Example II except that the catalyst that was tested herein only contained 80% zeolite Y and 20% alumina and had no tungsten compound on it. At the same temperature and under the same conditions no tetrahydrothiophene was formed during the test reaction.

EXAMPLE V—COMPARATIVE

This Example shows that a known hydrotreating catalyst will convert thiophene to hydrocarbons with splitting of the carbon-sulfur bond. One (1) g of Harshaw Co/Mo/$Al_2O_3$ catalyst No. HT-400 containing 3% CoO and 15% $MoO_3$ with a surface area of 200 $m^2/g$ and a pore volume of 0.45 cc/g was used. A stream of $H_2$ containing 9.5% thiophene was passed over the catalyst. The results are shown below:

TABLE 4

| Temp (°C.) | % Conversion Thiophene | Cumulative Time on Stream, Hrs. | % Hydrocarbons in Product | % THT in Product |
|---|---|---|---|---|
| 512 | 99.9 | 2 | 99 | 0 |
| 331 | 99.9 | 2.5 | 99 | 0 |
| 331 | 99.9 | 3.5 | 99 | 0 |
| 288 | 8.3 | 4 | 97.6 | 0.1 |
| 253 | 60.0 | 8 | 98.6 | 0.1 |
| 253 | 57.1 | 8.5 | 96.7 | 0.4 |
| 212 | 22.0 | 10.0 | 97.7 | 1.4 |

In the data depicted above, no tetrahydrothiophene was detected in the product in the first three runs, only 0.1% was detected in the next two runs, 0.4% was detected in the next run, and 1.4% was detected in the last run.

The results show that this catalyst has one substantial function, i.e., hydrodesulfurization of thiophene to hydrocarbons and hydrogen disulfide even at the relatively low temperatures of 200° C. to 300° C.

While the use of the catalysts of the present invention has been exemplified particularly in connection with the conversion of thiophene to tetrahydrothiophene, it is understood that these catalysts also find utility in the conversion of other unsaturated sulfur containing compounds including, but not limited to, the conversion of various other substituted and unsubstituted thiophenes and other similar compounds.

While a limited number of preferred embodiments of the present invention have been described and tested above, one skilled in the art will, nevertheless, recognize numerous substitutions, modifications and alterations which can be made without departing from the spirit and scope of the invention as limited by the following claims.

We claim:

1. A catalyst composition for the hydrogenation of an unsaturated sulfur-containing compound without appreciably breaking the carbon-sulfur bond comprising tungsten carbide and a mixture of zeolite and alumina.

2. A catalyst composition according to claim 1, useful for the conversion of thiophene to tetrahydrothiophene.

3. A catalyst composition according to claim 1, wherein the zeolite component is Zeolite A.

4. A catalyst composition according to claim 1, wherein the zeolite component is Zeolite Y.

5. A catalyst composition according to claim 1, wherein the catalyst comprises from about 1 to about 50 wt % tungsten carbide based upon the total weight of catalyst.

6. A catalyst composition according to claim 1, wherein the catalyst comprises from about 1 to about 50 percent by weight tungsten carbide and a zeolite selected from the group comprising Zeolite A and Zeolite Y, which catalyst composition is capable of selective effecting conversion of thiophene to tetrahydrothiophene without producing substantial quantities of sulfur and other hydrocarbon byproducts.

7. A catalyst composition according to claim 1, wherein the zeolite/$Al_2O_2$ ratio is between about 90/10 and 10/90.

8. A catalyst composition according to claim 1, wherein the zeolite/$Al_2O_3$ ratio is between 60/40 and 90/10.

9. A catalyst composition according to claim 1, wherein the zeolite/$Al_2O_3$ ratio is 80/20.

10. A catalyst composition according to claim 1, wherein the surface area is between about 30–800 $m^2/g$.

11. A catalyst composition according to claim 1, wherein the surface area is about 650 $m^2/g$.

12. A catalyst composition according claim 1, wherein the silica content is between 5–80%.

13. A catalyst composition according to claim 1, wherein the silica content is about 65%.

* * * * *